United States Patent
Heid et al.

(10) Patent No.: US 9,520,262 B2
(45) Date of Patent: Dec. 13, 2016

(54) X-RAY SOURCE, METHOD FOR PRODUCING X-RAYS AND USE OF AN X-RAY SOURCE EMITTING MONOCHROMATIC X-RAYS

(75) Inventors: Oliver Heid, Erlangen (DE); Timothy Hughes, Erlangen (DE); Jennifer Sirtl, Fürth (DE)

(73) Assignee: SIEMENS AKTIENGESELLSCHAFT (DE)

( * ) Notice: Subject to any disclaimer, the term of this patent is extended or adjusted under 35 U.S.C. 154(b) by 162 days.

(21) Appl. No.: 14/406,301

(22) PCT Filed: Jun. 14, 2012

(86) PCT No.: PCT/EP2012/061310
§ 371 (c)(1),
(2), (4) Date: Dec. 8, 2014

(87) PCT Pub. No.: WO2013/185827
PCT Pub. Date: Dec. 19, 2013

(65) Prior Publication Data
US 2015/0139402 A1    May 21, 2015

(51) Int. Cl.
*H01J 35/10*     (2006.01)
*H01J 35/08*     (2006.01)
(Continued)

(52) U.S. Cl.
CPC .............. *H01J 35/108* (2013.01); *A61B 6/484* (2013.01); *H01J 35/08* (2013.01); *H01J 35/24* (2013.01);
(Continued)

(58) Field of Classification Search
CPC   H01J 35/08; H01J 2235/081; H01J 2235/087; H01J 2235/084; H01J 35/108
See application file for complete search history.

(56) References Cited

U.S. PATENT DOCUMENTS

| | | | |
|---|---|---|---|
| 3,825,786 | A | 7/1974 | Einighammer et al. |
| 6,385,295 | B1 | 5/2002 | Van De Vorst et al. |

(Continued)

FOREIGN PATENT DOCUMENTS

| | | |
|---|---|---|
| CN | 1144015 A | 2/1997 |
| CN | 1287378 A | 3/2001 |

(Continued)

OTHER PUBLICATIONS

Fournier K. B. et al: Efficient multi-keV x-ray sources from Ti-doped aerogel targets; Proceedings of SPIE; vol. 5196; pp. 194-204; ISSN: 0277-786X; DOI: 10.1117/12.505872; XP055053984; Jan. 7, 2004.

(Continued)

*Primary Examiner* — Hoon Song
(74) *Attorney, Agent, or Firm* — Schmeiser Olsen & Watts LLP

(57) ABSTRACT

X-ray sources and production of X-rays, in particular, producing monochromatic x-rays is provided. More specifically, a method for producing X-rays and the use of the X-ray source for x-raying bodies (for example human bodies). An aerogel, for example in the form of a rod, may be provided in a housing as a target. Said target may be bombarded with an electron beam, the aerogel being vaporized due to the extreme low density and the high energy. As a result, the target is guided by means of a roller such that an unused target for producing, in particular, the monochromatic X-rays, is always available.

14 Claims, 3 Drawing Sheets

Figure 1:
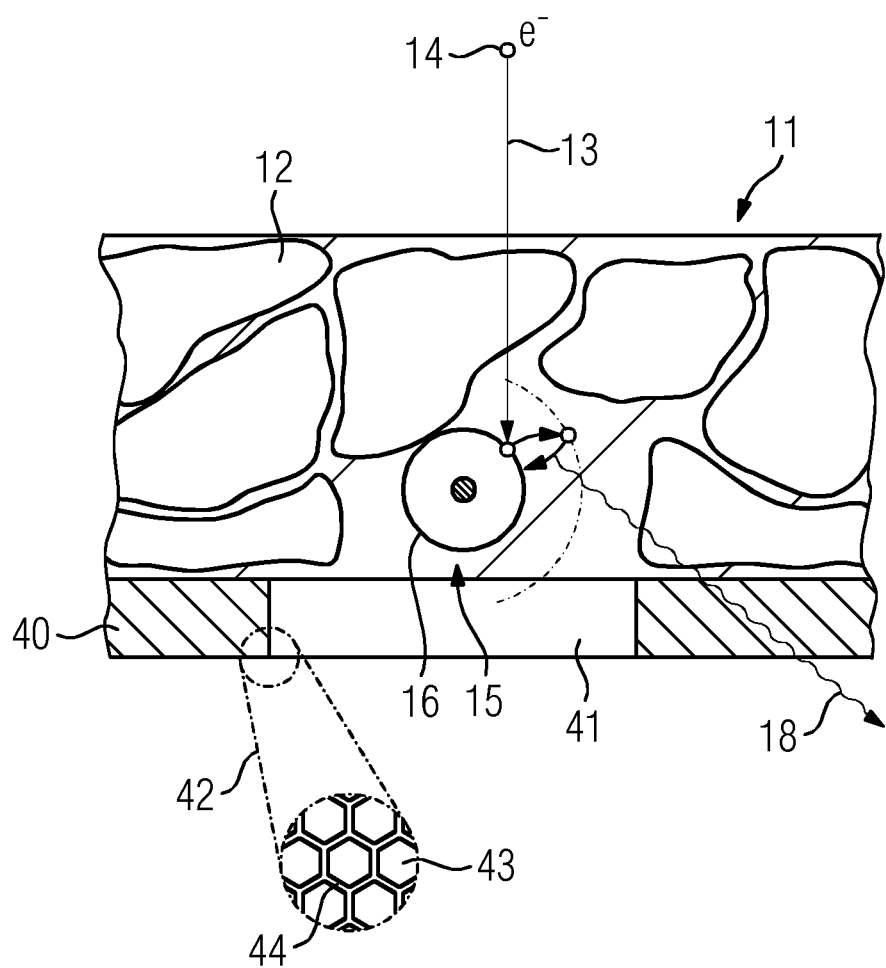

(51) Int. Cl.
*H01J 35/24* (2006.01)
*A61B 6/00* (2006.01)

(52) U.S. Cl.
CPC ..... *H01J 2235/081* (2013.01); *H01J 2235/084* (2013.01); *H01J 2235/1006* (2013.01)

(56) References Cited

U.S. PATENT DOCUMENTS

| | | |
|---|---|---|
| 7,313,226 B1 | 12/2007 | Falce et al. |
| 2002/0150213 A1 | 10/2002 | Poulsen |
| 2006/0133574 A1* | 6/2006 | Nagai ............... B82Y 10/00 378/119 |
| 2008/0019481 A1 | 1/2008 | Moy |
| 2008/0144774 A1 | 6/2008 | Antonis |
| 2012/0051496 A1 | 3/2012 | Wang et al. |
| 2012/0051498 A1 | 3/2012 | Koishi |

FOREIGN PATENT DOCUMENTS

| | | |
|---|---|---|
| CN | 1853252 A | 10/2006 |
| CN | 1971834 A | 5/2007 |
| CN | 101310359 A | 11/2008 |
| CN | 102013378 A | 4/2011 |
| DE | 102009007871 A1 | 8/2010 |
| EP | 0063190 A1 | 10/1982 |
| JP | H08194100 A | 7/1996 |
| JP | 2001256909 A | 9/2001 |
| WO | WO 0019496 A1 | 4/2000 |
| WO | WO 2004086467 A1 | 10/2004 |

OTHER PUBLICATIONS

International Search Report; PCT/EP2012/061310; International file Date: Jun. 14, 2012; 3 PGS.

\* cited by examiner

X-RAY SOURCE, METHOD FOR PRODUCING X-RAYS AND USE OF AN X-RAY SOURCE EMITTING MONOCHROMATIC X-RAYS

CROSS-REFERENCE TO RELATED APPLICATION

This application claims priority to PCT Application No. PCT/EP2012/061310, having a filing date of Jun. 14, 2012, the entire contents of which is hereby incorporated by reference.

FIELD OF TECHNOLOGY

The following relates to an X-ray source having a housing in which a target is provided that can emit X-rays when being bombarded with an electron beam. The disclosure additionally relates to a method for producing X-rays, in which in the housing of an X-ray source, a target is bombarded with an electron beam and X-rays are emitted. The disclosure moreover relates to the use of an X-ray source emitting monochromatic X-rays.

BACKGROUND

An X-ray source, the use thereof and a method for producing X-rays of the type mentioned in the introduction are disclosed, for example, in US 2008/0144774 A1. According to said document, an X-ray source can be configured by way of example by arranging electrodes within a housing. An electrode having a potential of 0 volts (V) produces an electron beam in the housing. An anode, which is used as a target for the electron radiation, is arranged opposite said electrode. Said anode is at 100 kV. Located downstream of the anode is furthermore a collector which is at a potential of 10 kV. When the electron beam strikes the anode, X-rays are released which can be coupled out of the housing through a suitable window (transparent to X-rays) and can be supplied for use.

The anode serving as a target must be configured as a thin-walled structure since monochromatic X-rays are produced only in the top few atomic layers. A thicker target results in increasing, undesired production of bremsstrahlung (braking radiation, i.e. electromagnetic radiation produced by a sudden slowing down or deflection of charged particles (especially electrons) passing through matter in the vicinity of the strong electric fields of atomic nuclei). By way of example, the anode may have a base plate made of boron, having a thickness of between 10 and 200 µm. A thin layer of tungsten having a layer thickness of 100 to 500 nm, which is used as a target, is applied on said base plate. However, the very thin tungsten layer is exposed to a high thermal load on account of the electron beam.

SUMMARY

An aspect relates to the X-ray source mentioned above, such that a relatively long operating time of the X-ray source is possible without the target needing to be replaced. It is an additional aspect to specify a method for operating said X-ray source. Finally, another aspect is to find a use for such an X-ray source.

The aspect is achieved by way of the X-ray source specified above by using an aerogel as the target material. The aerogel has an extremely low density on account of pores formed in a network of the aerogel material having very thin walls (like a foam). The electron beam of the X-ray source penetrates said active medium formed by the aerogel and excites the K-shell of the atoms of the aerogel material. As soon as the electrons of the atoms return from their excited state to the K-shell, the energy is emitted in specific quanta as monochromatic X-rays. On account of the very low density of the aerogel, no bremsstrahlung, or only very little bremsstrahlung is produced, with said bremsstrahlung (if at all present) propagating in the direction of the electron beam, which is therefore easy to separate from the monochromatic X-rays. As a result, the undisturbed monochromatic X-rays can be supplied to the desired use (for example for a medical purpose).

According to one embodiment, the aerogel is fixed on a metal foil made of a light metal or a plurality of light metals (an alloy), preferably aluminum. The aerogel is vulnerable to mechanical stress on account of its very low density, and the carrier foil with its carrier structure therefore contributes to its stabilization. The carrier foil itself must be of sufficiently thin configuration for as little bremsstrahlung as possible to be produced and so that said bremsstrahlung maintains its direction according to the orientation of the electron beam. The metal foil should preferably have a thickness of 0.5 µm to 10 µm, preferably 1 µm, if no perforated carrier is used. If the carrier foil is a perforated foil, the metal foil can also be of a significantly thicker and thus mechanically more stable configuration, since it makes no contribution to the emitted radiation. In this embodiment, the metal foil can advantageously have holes which are bridged by the target material. In this way, it is also possible to use thicker foils, with the latter forming a grid-like supporting structure. The holes can be, for example, round holes arranged in a regular pattern. In this way, a regular grid structure is produced. It is particularly advantageous if the holes have the cross section of a regular hexagon and are arranged in the form of honeycombs in the metal foil. This results in a supporting structure of webs arranged in a honeycomb pattern (corresponding to the plan view of a honeycomb). In this case, it is possible, with advantageously as little material outlay as possible, to achieve maximum supporting effect. In the process, the production of bremsstrahlung is advantageously largely avoided. During the production of the monochromatic X-rays, it is accepted that the target is thermally destroyed.

If the target is in the form of a foil (reinforced or not reinforced), it is particularly advantageous if the target is configured as a tape which can be unwound from a first roller and be wound onto a second roller. The tape-type configuration of the anode has the great advantage that it can be guided past the electron beam by simple handling steps. As a result, a relative movement between the target and the electron beam can be produced. It is particularly advantageous to supply the tape in the form of a roller to the X-ray source and to wind up the used-up tape onto a corresponding roller such that it is easily possible during operation of the X-ray source to reliably store the tape in the housing and supply it to the electron beam. In addition, once the tape is used up, it can be replaced simply by removing the rollers. Particularly advantageous, a provision may be made for this purpose for the first roller and the second roller to be accommodated in vacuum locks of the housing. A vacuum lock within the context of the application may be understood to be a separate closed-off space within the housing, wherein the space has a through-passage for the tape-type target material toward the interior of the housing. Also present are closable lock openings toward the outside, through which the used rollers fit. A roller can then be replaced through venting only the available lock chambers, such that the remaining housing space of the housing remains evacuated. It should be noted in this context that the production of X-rays preferably takes place in an evacuated housing. At least the second roller should advantageously also be coupled mechanically to a drive shaft which is preferably attached on the outside of the housing. Attaching it on the outside of the housing has the advantage that the drive shaft can be maintained relatively easily since it is easily accessible and maintenance work does not necessitate the venting of the housing space.

Another possibility of ensuring a relative movement between an electron beam and the target material is to give the production device for the electron beam a pivotable design. By pivoting the production device, the electron beam also moves to and fro on the target material, as a result of which uniform exposure of the entire target material is possible. Of course, a pivotable production device can also be combined with a roller mechanism. While the roller mechanism can effect a movement of the electron beam on the tape in the direction of the winding direction, the production device can be pivotable, in particular, perpendicular to the movement direction of the tape. This ensures that the tape can also be utilized over its full width, as a result of which it is possible to utilize the target material in an optimum fashion.

One alternative embodiment of the invention makes a provision for the aerogel to be in the form of a rod and for it to be capable of being guided through the electron beam using a guide apparatus. The rod can advantageously have a cross section which is suitable for being penetrated completely by the electron beam. In this variant, guiding the electron beam is not necessary. Once the aerogel is used up, the rod can be moved by the guide apparatus such that unused material can be brought into the influence region of the electron beam. The rod form can advantageously be produced very easily. Advantageously, the rod form can be stored, with its own elasticity being taken into account, on a roller, which is arranged at the other end of the guide apparatus. By unwinding the roller, the rod of the aerogel is automatically supplied by the guide apparatus, wherein the guide apparatus can, at the same time, contribute to a straightening of the rod material.

According to one advantageous embodiment, a provision is made for the aerogel to be made of a material, wherein the K-shell of the atoms of which has an emission characteristic which is usable for the application. Specifically, said definition applies to the following light metals: all alkaline metals, scandium, yttrium, titanium, aluminum and all earth alkaline metals except for radium. Further advantageous material groups for forming the aerogel are tungsten, molybdenum and the group of the lanthanides. Specifically, this is the element lanthanum and the 14 elements following lanthanum in the periodic table, including Ce, Pr, Nd, Pm, Sm, Eu, Gd, Tb, Dy, Ho, Er, Tm, Tb and Lu.

The use of the aerogel also has the advantage that monochromatic X-rays can advantageously be produced on account of excitation of the target using the electron beam. These are X-rays having only one wavelength, which has the advantage that X-radiographs can be imaged more sharply with monochromatic X-rays, for example. For this reason, an alternative way of achieving the embodiment of the invention is also to use said monochromatic X-rays for x-raying a body, wherein the body must be of a nature such that, at the wavelength of the used, the monochromatic X-rays contrast with body appearing on the image. The body may be a mechanical structure (mechanical or inanimate body), such as for example a component connection that is to be examined for ingress of air. Another possibility is to record X-radiographs of a human or animal body.

BRIEF DESCRIPTION

Figure 2:
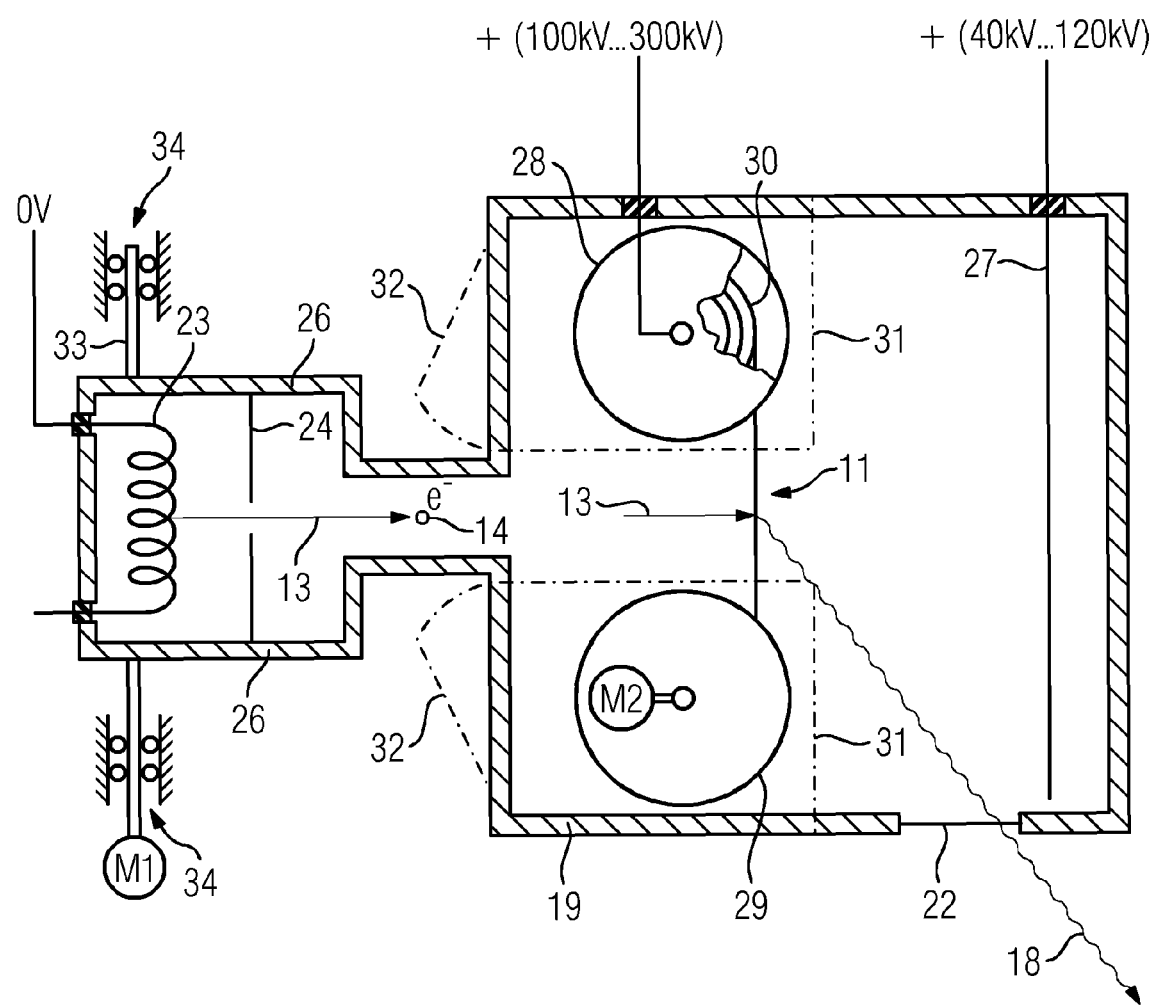
Figure 3:
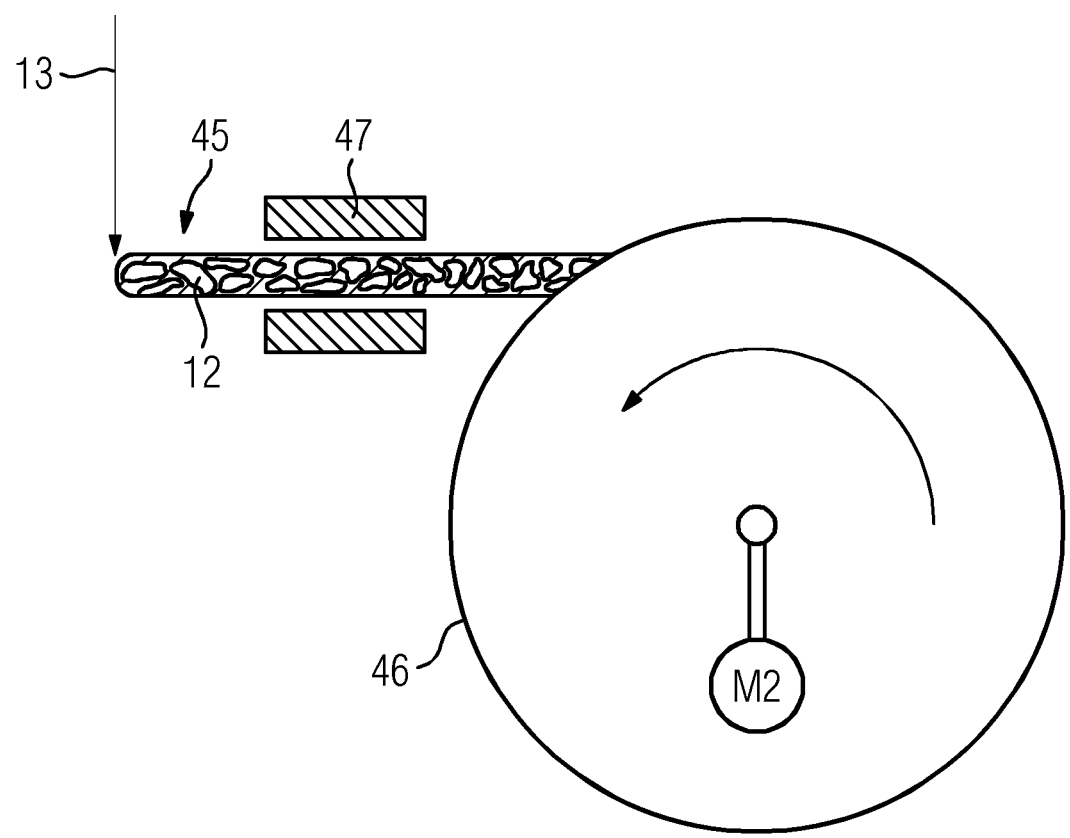

Some of the embodiments will be described in detail, with reference to the following figures, wherein like designations denote like members, wherein:

FIG. 1 schematically illustrates an embodiment producing monochromatic X-rays in a foil made of an aerogel in a schematic section, FIG. 2 shows an exemplary embodiment of the X-ray light source, in which the foil according to FIG. 1 is used, in schematic section, and FIG. 3 shows another exemplary embodiment of a target material in the form of a rod for the X-ray source.

DETAILED DESCRIPTION

In FIG. 1, an aerogel 12 (illustrated as a detail) is provided as the target 11. An electron beam 13 strikes, with electrons 14, an atom 15 of the target material (for example lanthanum). Also illustrated is the K-shell 16 of the atom 15, wherein the electron beam causes excitation of one of the electrons 17 of the K-shell 16 and raises it up to a different shell. When these electrons jump back, monochromatic X-rays 18 are emitted in the process.

The aerogel 12 is applied on a metal foil 40 which supports the aerogel 12. Said metal foil 40 moreover has holes 41, which can be arranged in a regular pattern in the metal foil 40 in order to ensure as low a material density/ atom layer number as possible while maintaining as great a supporting effect of the metal foil 40 as possible. As can be seen in a sectional illustration 42 (plan view of the metal foil), the holes 41 can have, in particular, the form of honeycombs 43. The material of the metal foil 40 is then configured in the form of webs 44. The width of the webs can be determined structurally taking into account the necessary supporting effect.

FIG. 2 shows the construction of the X-ray source according to embodiments of the invention. The X-ray source itself is housed in an evacuable housing 19 which has a window 22. The electron beam strikes the target 11, wherein said target absorbs hardly any energy of the electron beam owing to its low thickness. However, part of the energy is converted, owing to an excitation of the atoms 15 (see FIG. 1) in the already described manner, into monochromatic X-rays 18 which can leave the housing through the window 22.

The electron beam penetrating the target is electrostatically decelerated by the collector to the extent that the electrons of the electron beam impact the collector with a low energy such that no bremsstrahlung can be produced. In order to accelerate the electrons 14 in the electron beam 13 sufficiently, what is known as an e-gun (i.e. an electron gun) can be provided. Said e-gun has a heated cathode 23 which emits electrons if an electrical field is present. Said electrons are bundled using an electrical lens 24 so that the electron beam produces as small a punctiform radiation source as possible on the target. The electrical field is established by switching the target as an anode. Said anode can be operated at a potential of 100 to 300 kV, wherein a collector 27 at a potential of 40 to 120 kV is additionally used downstream of the target.

Also provided in the housing are a first roller 28 and a second roller 29. The target according to FIG. 1, which is present in the form of a tape 30, is wound onto the first roller 28 and is actuated in a manner which is not illustrated further using an actuator M2 (located outside the housing in a manner known per se on a drive shaft for rotating the roller 29). In the process, the target 11 is unwound from the roller 28 and re-wound onto the roller 29. To permit simple replacement of the rollers 28, 29, vacuum locks 31, which are indicated in dashed-dotted lines, are provided such that the remaining space of the housing need not be vented when the rollers 28, 29 are replaced. The rollers 28, 29 are removed through the indicated doors 32.

The electron gun is likewise mounted pivotably via a shaft 33. It is driven using a motor M1. The shaft 33 is parallel to the plane of the drawing in mounts 34, such that by pivoting the electron gun, the electron beam 13 can be pivoted over the entire width of the tape 30. The effect of the driving of the rollers 28, 29 is that the electron beam can also change the point of impact on the target in the direction of the longitudinal extent of the tape 30.

FIG. 3 illustrates a target in the form of a rod 45. Said target is wound onto a storage roller 46 having a sufficiently large diameter for the deformation due to the diameter of the roller 46 not to damage the aerogel 12 of the target, in particular deforms only elastically. Using a guide apparatus 47, the target 45 is supplied to the electron beam 13. Here, the motor M2 is used in the manner described in FIG. 2. As opposed to FIG. 2, a further roller for winding the target up is not necessary, since the target evaporates when irradiated with the electron beam 13. Also envisaged, however, may be the mounting of the apparatus according to FIG. 3 in the X-ray source according to FIG. 2 by using it instead of roller 28. In this case, roller 29 is not used.

The invention claimed is:

1. An X-ray source having a housing in which a target is provided that can emit X-rays when the target is bombarded with an electron beam, wherein the target includes a target material, wherein said target material is an aerogel.

2. The X-ray source as claimed in claim 1, wherein the aerogel is fixed on a metal foil made of a light metal or a plurality of light metals.

3. The X-ray source as claimed in claim 2, wherein the metal foil has a thickness of 0.5 µm to 10 µm.

4. The X-ray source as claimed in claim 2, wherein the metal foil has holes which are bridged by the target material.

5. The X-ray source as claimed in claim 4, wherein the holes are arranged in a regular pattern.

6. The X-ray source as claimed in claim 5, wherein the holes have the cross section of a regular hexagon and are arranged in a form of honeycombs in the metal foil.

7. The X-ray source as claimed in claim 1, wherein the target is configured as a tape which can be unwound from a first roller and wound onto a second roller.

8. The X-ray source as claimed in claim 1, wherein the aerogel is in a form of a rod and can be guided through the electron beam using a guide apparatus.

9. The X-ray source as claimed in claim 1, wherein at least one lanthanide is included in the target material.

10. The X-ray source as claimed in claim 2, wherein the metal foil is made of aluminum.

11. A method for producing X-rays, comprising the steps of:
providing a housing having an X-ray source, producing an electron beam;
bombarding a target with the electron beam, wherein the target includes an aerogel target material; and
emitting X-rays from the target.

12. The method as claimed in claim 11, wherein monochromatic X-rays are emitted from the target.

13. The method as claimed in claim 11, further comprising the step of supplying a new target material of the aerogel when the target material is used up by the electron beam.

14. A method for X-raying a body comprising the steps of:
providing a housing having a X-ray source, producing an electron beam;
bombarding a target with the electron beam, wherein the target includes a target material comprised of an aerogel;
emitting monochromatic X-rays from the target, producing differentiable contrasts at the wavelength of the X-rays used than the body being imaged.

* * * * *